United States Patent [19]

Woods

[11] Patent Number: 4,817,636

[45] Date of Patent: Apr. 4, 1989

[54] ANTI-SNORING DEVICE

[76] Inventor: Thomas H. Woods, 2920 Marshall St., Falls Church, Va. 22042

[21] Appl. No.: 103,295

[22] Filed: Oct. 1, 1987

[51] Int. Cl.⁴ ............................................. A61F 5/56
[52] U.S. Cl. .................................................... 128/848
[58] Field of Search .................................. 128/136, 163

[56] References Cited

U.S. PATENT DOCUMENTS

| | | | |
|---|---|---|---|
| 1,354,652 | 10/1920 | Jefferies | 128/848 |
| 1,629,892 | 5/1927 | Storms | 128/136 |
| 1,775,718 | 9/1930 | Garvey | 128/136 |
| 2,627,268 | 2/1953 | Leppich | 128/136 |
| 4,711,237 | 12/1987 | Kaiser | 128/136 |

Primary Examiner—Richard J. Johnson
Assistant Examiner—Kevin G. Rooney
Attorney, Agent, or Firm—Foley & Lardner, Schwartz, Jeffery, Schwaab, Mack, Blumenthal & Evans

[57] ABSTRACT

An anti-snoring device comprising a sheet of flexible, tear-resistant material, a hypoallergenic adhesive applied to the back face of the material, and a protective backing sheet covering the adhesive back of said material, wherein the device is adapted to cover a user's mouth completely, has sides which converge towards the top to conform to the user's cheeklines, and a top which has a central depression to conform to the user's nose and nostrils.

8 Claims, 2 Drawing Sheets

ANTI-SNORING DEVICE

BACKGROUND OF THE INVENTION

The present invention relates to a device for prevention of snoring. It is generally accepted that snoring results from vibrations of the soft palate and uvula when air is breathed in through the mouth. If intake of air through the mouth can be prevented, then snoring can also be prevented.

Existing devices for prevention of snoring or air intake through the mouth require the insertion of such devices in the mouth or in the nose, or require the use of straps tied around the head or neck so as to hold such devices in place. Such devices are uncomfortable and are not widely accepted.

A device to prevent intake of air through the mouth which does not require insertion of a foreign object into the mouth or nose or the use of straps is disclosed by U.S. Pat. No. 1,354,652. This device is a rectangular piece of material provided with slits along the top and bottom and cut-outs at the sides and has an adhesive backing to retain it in place when it is being used to cover the mouth. A major drawback of this device is that its length extends across a person's cheeks when in use, such that movement of the cheek muscles causes discomfort or causes the device to loosen and fall off during sleep.

SUMMARY OF THE INVENTION

It is therefore an object of the present invention to provide an anti-snoring device which can be applied externally over the user's mouth without requiring insertion of a foreign object into the user's mouth or nose, without requiring the use of straps to retain the device in place and does not impair the user's facial movement.

It is another object of the present invention to provide an anti-snoring device which conforms to the area bounded by a user's nose and cheeklines such that it can be worn with minimal discomfort.

It is a further object of the present invention to provide an anti-snoring device which is more readily retained in place during use.

It is also an object of the present invention to provide an anti-snoring device which is economical so that it can be discarded after each use.

In accomplishing these and other objects, there has been provided in accordance with one aspect of the present invention, an anti-snoring device comprising a sheet of flexible, tear-resistant material, a hypoallergenic adhesive applied to the back face of said material, and a backing sheet which covers the adhesive back of said material, wherein the device is adapted to cover a user's mouth completely, has sides converging towards the top to conform to the cheeklines of the user, and has a central depression at the top to conform to the user's nose.

In accordance with another aspect of the invention, there is provided an anti-snoring device as above, wherein the point at which each side and the lower edge of the device meet is cut off.

Further objects, features and advantages of the present invention will become apparent from the following detailed description. It should be understood, however, that the detailed description, while indicating preferred embodiments of the invention, is given by way of illustration only, since various changes and modifications within the spirit and scope of the invention will become apparent to those skilled in the art from this detailed description.

DETAILED DESCRIPTION OF PREFERRED EMBODIMENTS

Figure 1:
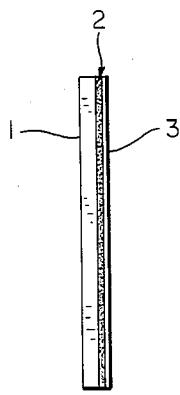
FIG. 1 is an end view of an anti-snoring device according to the invention.

This invention is an anti-snoring device which comprises a sheet of material 1 which has a layer of hypoallergenic adhesive 2 on its back face, i.e., the side to be applied to the user's mouth, and a strippable protective backing sheet 3 covering the adhesive back face, as shown in FIG. 1.

Figure 2:
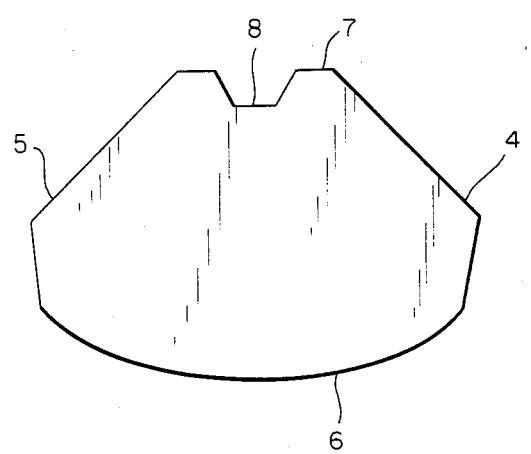
FIG. 2 is a plan view of the anti-snoring device.
Figure 3:
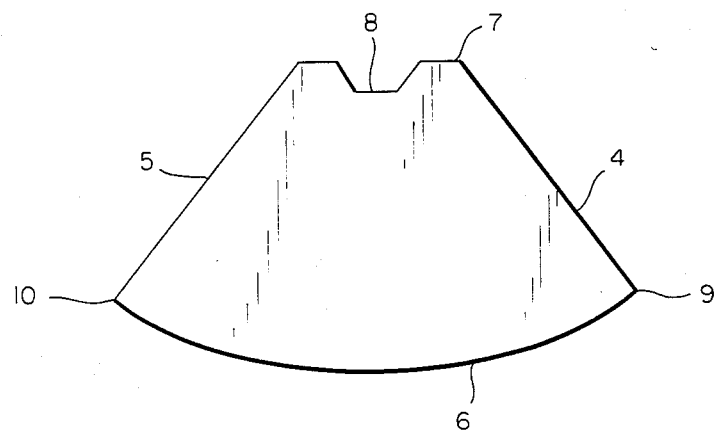
FIG. 3 is a plan view of an alternative design of the anti-snoring device.

This device is designed to accommodate a user's facial muscles around the mouth and nostrils to facilitate good adhesion between the device and the face of a user. As shown in FIGS. 2 and 3, the device's shape is such that when applied, it completely covers the user's lips, its angular sides 4 and 5 lie along and below the user's cheeks, its lower edge 6 lies below and is continuously curved to generally follow the contour of the user's lower lip, its upper edge 7 lies above the user's upper lip but below the user's nose and has a central depression 8 which follows the contour of the user's nose in the area of the nostrils. Preferably, the points 9 and 10 (FIG. 3) at which the angular sides and the lower edge meet are cut off to form straight edges 12 and 13 (FIG. 2) to prevent the points from irritating the user's face. Optionally, however, such points may be left in place, as shown in FIG. 3, for ease of manufacture.

The size of the device is about two inches high and three inches wide, as viewed in place over the mouth of a user standing in an erect position. It is contemplated that this device can be manufactured in smaller or larger sizes to accommodate extreme differences in a user's mouth size, although the aforementioned two-inch by three-inch size should be satisfactory for the vast majority of users.

The device is made of a sheet of material, preferably paper or non-woven fabric, which is thin and flexible, yet strong enough to withstand tearing when in use, when it is peeled from its protective backing sheet and when an adhesive is applied to its back face. If desired, the material may be fiber reinforced for extra strength and tear-resistance.

Figure 4:
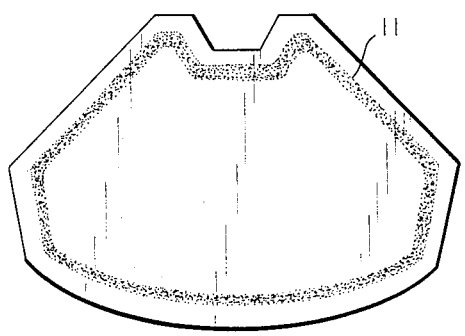
FIG. 4 is a plan view of an alternate anti-snoring device showing distribution of adhesive around the edges of the device.

An adhesive, preferably a sterile, pressure-sensitive, hypoallergenic adhesive is applied as a film on the back face of the sheet of material. Preferably, the adhesive is applied uniformly over the entire back surface of the sheet of material. In the alternative, the adhesive can be applied over only a portion of the sheet of material, for example, around the outer edges 11 as shown in FIG. 4. The adhesive is of such a character that it is non-drying, is capable of remaining in a tacky state, and yet can be readily removed from a user's skin without injury to the user. Conventional silicone adhesives, such as those used for adhesive bandage strips, may be used in this invention. Prior to use, the adhesive backing of the device is covered by a protective backing sheet.

The backing sheet, preferably made of paper, can be coated on its inner face, i.e., the face to be attached to the adhesive, so that the device can easily be peeled off the backing sheet and so that very little adhesive will come off on the backing sheet. The backing sheet is of a size large enough to cover the back face of the device, and optionally, can be made in the same size and shape as the device. In the latter instance, the backing sheet may be split to facilitate removal of the backing sheet when the device is used.

Optionally, after manufacture, the device can be placed in a suitable package and be sterilized in a conventional manner for sanitation purposes.

For convenience, a commercially available non-woven material which has a hypoallergenic adhesive coating on its back face and a protective backing sheet covering the adhesive, for example, MICROPORE TM tape material from 3M Corporation (St. Paul, Minn.), can be used to produce the anti-snoring device.

Figure 5:
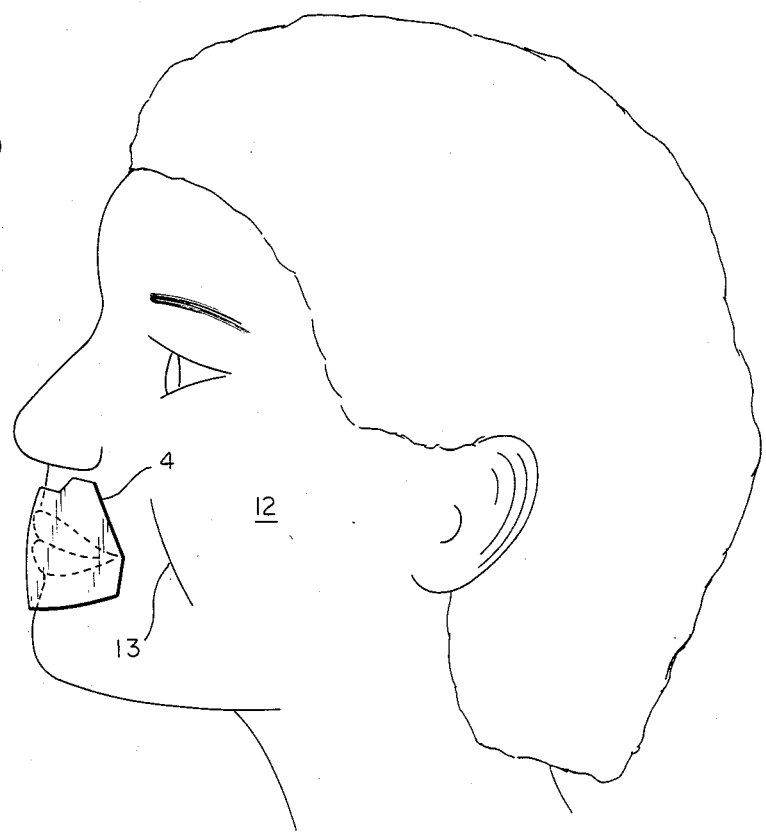
FIG. 5 is a frontal view of the anti-snoring device when applied to cover a user's mouth.
Figure 6:
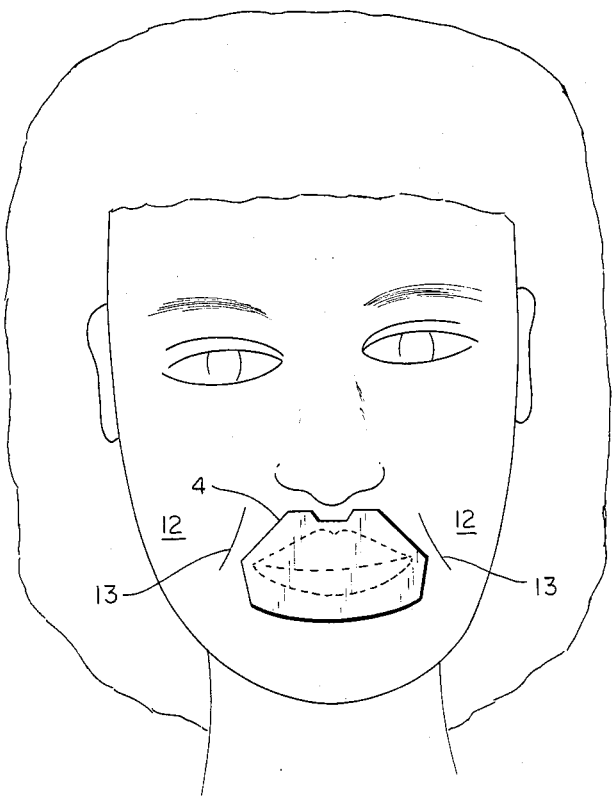
FIG. 6 is a side view of the anti-snoring device of FIG. 5 when applied to cover the user's mouth.

Immediately prior to use of the device, the mouth and nose area of the user must be cleansed with an oil-removing substance, for example, soap and water, or rubbing alcohol. The user's nasal passage must be cleared for breathing, and the mouth should be in a closed position. The device is then peeled from its protective backing sheet and fitted on the user's face so that the adhesive backing is against the user's face and the device completely covers the user's mouth. As shown in FIGS. 5 and 6, the angular sides 4 of the device should lie below the user's cheeks 12 and extend along the user's cheekline 13, and its upper edge should lie below and along the contours of the nose and nostrils. As used herein the term "cheeklines" refers to the course of the fleshy tissue folds which define the lines of demarcation between the mouth area and the cheek areas of the human face. The device is then pressed against the user's lips and face to facilitate adherenoe. If the protective backing sheet is provided with a slit, the device can first be fitted to the user's face and held in position before first one end and then the other of the backing sheet are removed. Any minor discomfort, for example, as caused by an improper fit or because the user is unused to having a sheet over the user's mouth can be ameliorated by removing and reapplying the device several times.

Such an anti-snoring device can be used to stop all apnea sounds, i.e., snoring, and may be useful for people who have asthma since the device encourages breathing through the nose which is equipped to remove foreign particles from the air inhaled.

It has been found that most people using this device can stop snoring in one to three days. Long-term snorers or mouth-breathers may require seven to ten days to overcome this habit.

What is claimed is:

1. An anti-snoring device comprising a sheet of flexible, tear-resistant material, a hypoallergenic adhesive applied to the back face of said material, and a backing sheet which covers the adhesive back of said material, wherein the device is sized and configured to substantially cover a user's closed mouth and fit within the area between the cheeklines and underneath the nose without extending over the user's nose or cheeks and to extend below the user's mouth sufficiently to hold the mouth closed, said device having angular sides converging towards the top edge to extend along the cheeklines o f the user, and having a central depression at the top edge to fit below the underside of the user'nose.

2. An anti-snoring device according to claim 1, wherein the point at which each side and the lower edge of the device meet is cut off.

3. An anti-snoring device according to claim 2, wherein the lower edge of said device is continuously convexly curved to generally conform to the contour of the user's lower lip.

4. An anti-snoring device according to claim 2, wherein said material is a non-woven fabric.

5. An anti-snoring device according to claim 2, wherein said material is paper.

6. An anti-snoring device according to claim 1, wherein said adhesive is uniformly applied to the back face of said material.

7. An anti-snoring device according to claim 2, wherein said adhesive is applied to the outer edges of said material.

8. An anti-snoring device according to claim 2, wherein the overall dimensions of the device measure about two inches by three inches.

* * * * *